(12) United States Patent
Swain et al.

(10) Patent No.: US 7,288,074 B2
(45) Date of Patent: Oct. 30, 2007

(54) GUIDE WIRE STRUCTURE FOR INSERTION INTO AN INTERNAL SPACE

(75) Inventors: Paul Christopher Swain, London (GB); Gary L. Long, Gerards Cross (GB)

(73) Assignees: UCL Business PLC, London (GB); Ethicon Endo-Surgery, Inc., Cincinnati, OH (US)

( * ) Notice: Subject to any disclaimer, the term of this patent is extended or adjusted under 35 U.S.C. 154(b) by 527 days.

(21) Appl. No.: 10/409,270

(22) Filed: Apr. 8, 2003

(65) Prior Publication Data
US 2004/0199087 A1   Oct. 7, 2004

(30) Foreign Application Priority Data
Apr. 3, 2003   (GB) .................. 0307715.3

(51) Int. Cl.
*A61B 5/00* (2006.01)
*A61M 25/00* (2006.01)
(52) U.S. Cl. ...................................... 600/585
(58) Field of Classification Search ............. 600/433, 600/434, 435, 585; 604/164.01, 164.13
See application file for complete search history.

(56) References Cited

U.S. PATENT DOCUMENTS

| | | | |
|---|---|---|---|
| 3,791,387 A * | 2/1974 | Itoh | ............ 606/113 |
| 4,176,662 A | 12/1979 | Frazer | |
| 4,207,872 A | 6/1980 | Meiri et al. | |
| 4,326,530 A | 4/1982 | Fleury, Jr. | |
| 4,447,227 A | 5/1984 | Kotsanis | |
| 5,078,716 A | 1/1992 | Doll | |
| 5,337,732 A | 8/1994 | Grundfest et al. | |
| 5,345,925 A | 9/1994 | Allred, III et al. | |

(Continued)

FOREIGN PATENT DOCUMENTS

EP   0667115 A1   1/1995

(Continued)

OTHER PUBLICATIONS

Technical Advances and Experimental Devices for Enteroscopy, pp. 1052-5157, Charles Alexander Mosse, BA, MSC and C. Paul Swain, MD, vol. 9, No. 1, Jan. 1999.

(Continued)

*Primary Examiner*—Max Hindenburg
*Assistant Examiner*—Jonathan Foreman
(74) *Attorney, Agent, or Firm*—Victor Moreno (57) ABSTRACT

A method is described of inserting guide wires into a lumen, for example into the human gastrointestinal tract. A guide wire structure is employed which comprises at least two guide wires each having a leading end portion which terminates in a leading end, the guide wires being connected to one another by a junction at or adjacent their leading ends, the guide wires have a first position in which the leading end portions are substantially parallel to one another, a second position in which the leading end portions are curved, and a third position in which at least one of the leading end portions forms a loop. The guide wire structure is steered through the gastrointestinal tract by selectively advancing or retracting a single guide wire or advancing more than one guide wire simultaneously, according to the path which is required to be followed.

14 Claims, 8 Drawing Sheets

U.S. PATENT DOCUMENTS

| | | | |
|---|---|---|---|
| 5,398,670 A | 3/1995 | Ortiz et al. | |
| 5,522,819 A | 6/1996 | Graves et al. | |
| 5,595,565 A | 1/1997 | Treat et al. | |
| 5,604,531 A | 2/1997 | Iddan et al. | |
| 5,730,704 A | 3/1998 | Avitall | |
| 5,836,947 A | 11/1998 | Fleischmann et al. | |
| 5,879,295 A * | 3/1999 | Li et al. | 600/373 |
| 6,007,482 A | 12/1999 | Madni et al. | |
| 6,162,171 A | 12/2000 | Ng et al. | |
| 6,190,382 B1 | 2/2001 | Ormsby et al. | |
| 6,203,525 B1 | 3/2001 | Whayne et al. | |
| 2004/0030259 A1* | 2/2004 | Dae et al. | 600/549 |

FOREIGN PATENT DOCUMENTS

| | | |
|---|---|---|
| EP | 0827 712 A2 | 11/1999 |
| WO | WO94/05200 | 3/1994 |
| WO | WO98/11896 | 3/1998 |
| WO | WO98/19608 A1 | 5/1998 |
| WO | WO99/30610 | 6/1999 |
| WO | WO99/34726 | 7/1999 |
| WO | WO99/53827 | 10/1999 |
| WO | WO 00/22975 | 4/2000 |
| WO | WO 00/44275 | 8/2000 |
| WO | WO 01/08548 A1 | 2/2001 |
| WO | WO 01/67967 A | 9/2001 |

OTHER PUBLICATIONS

International Search Report dated Aug. 26, 2004, for related Application No. PCT/US2004/009982.

EPO Communication dated Jun. 7, 2004 for corresponding patent applications, European Patent Application No. 02257750.6.

* cited by examiner

GUIDE WIRE STRUCTURE FOR INSERTION INTO AN INTERNAL SPACE

RELATED APPLICATIONS

This application claims priority to and incorporates by reference Great Britain Patent Application Ser. No. 0307715.3 filed Apr. 3, 2003 and having the same title.

BACKGROUND

This invention relates to a guide wire structure for insertion into an internal space defined by a wall. The invention is particularly concerned with a guide wire structure which can be inserted into an interior space within a human or animal body. More particularly, it concerns a guide wire device which can be inserted into, and moved along, a lumen within the body of a human patient, for example within the gastrointestinal (GI) tract of a human patient.

A physician typically accesses and visualizes tissue within a patient's gastrointestinal (GI) tract with a long, flexible endoscope. For the upper GI, a physician may insert a gastroscope into the sedated patient's mouth to examine and treat tissue in the esophagus, stomach, and proximal duodenum. For the lower GI, a physician may insert a colonoscope through the sedated patient's anus to examine the rectum and colon. Some endoscopes have a working channel, typically about 2.5-3.5 mm in diameter, extending from a port in the handpiece to the distal top of the flexible shaft. A physician may insert medical instruments into the working channel to help diagnose or treat tissues within the patient. Physicians commonly take tissue biopsies from the mucosal lining of the GI tract using a flexible, biopsy forceps through the working channel of the endoscope.

Insertion of a flexible endoscope, especially into the colon, is usually a very time-consuming and uncomfortable procedure for the patient, even when sedated with drugs. A physician often needs several minutes to push a flexible endoscope through the convoluted sigmoid, descending, transverse, and ascending portions of the colon. The physician may diagnose and/or treat tissues within the colon either during insertion or removal of the endoscope. Often the flexible endoscope "loops" within the colon, such as at the sigmoid colon or at the splenic flexure of the colon, so that it becomes difficult to further advance the endoscope along the colon. When a loop is formed, the force exerted to push the scope stretches the mesentery and causes pain for the patient. Depending on the anatomy of the patient and the skill of the physician in manipulating the flexible endoscope, some portions of the colon may be unexamined, thus increasing the risk of undiagnosed disease. Given® Engineering LTD, Yogneam, Israel, sells a device in the U.S. called the M2A™ Swallowable Imaging Capsule. The device contains a tiny video camera, battery, and transmitter. It is propelled through the gastrointestinal tract by natural peristalsis. The device is currently used for diagnostic purposes and passes through the intestinal tract with a velocity determined by the natural, peristaltic action of the patient's body. PCT publication No. WO 01/08548 describes a self-propelling device adapted to travel through a passage having walls containing contractile tissue. The applicants disclose that the device is particularly useful as an enteroscope and may also carry objects such as feeding tubes, guide wires, physiological sensors or conventional endoscopes within the gut. A summary of other alternative to push endoscopy can be found in "Technical Advances and Experimental Devices for Enteroscopy" by C. Mosse, et al, published in Gastrointestinal Endoscopy Clinics of North America, Volume 9, Number 1, January 1999: pp. 145-161.

Guide wires have been used to aid the introduction of catheters and other instruments into many sites in the human body. Many medical applications and specific designs of guide wires have been for cardiovascular use. There are, however, specific challenges relates to the use of guide wires in the GI tract, as opposed to the vascular system. Thus, the bowel is more tortuous, softer and generally of larger diameter. Furthermore, in the case of the small intestine and the colon, these are longer than most arteries or veins. It is an object of an aspect of the invention to provide a guide wire structure which is capable of being advanced along the GI tract, and which, under appropriate conditions and with sufficient medical skill, can be used safely even when passing through complex looped formations of small intestine.

SUMMARY

According to the present invention, there is provided a guide wire structure for insertion into an interior space defined by a wall, the guide wire structure comprising at least two guide wires each having a leading end portion which terminates in a leading end, the guide wires being connected to one another at or adjacent their leading ends, the guide wires have a first position in which the leading end portions are substantially parallel to one another, a second position in which the leading end portions are curved, and a third position in which at least one of the leading end portions forms a loop. It is to be understood that, as used herein, the term "loop" does not necessarily denote a complete loop, but also includes a partial loop. It is also to be understood that the two guide wires (or, where there are more than two guide wires, any two of the guide wires) may be in the form of a continuous piece of guide wire material whose two ends are brought together where the connection is formed.

A primary purpose of the above structure is for insertion into an interior space within a human or animal body, for example into the GI tract of a human patient. It is believed that the guide wire structure of the present invention should be capable of being negotiated through the small intestine or colon, and may allow the delivery of endoscopic devices even to relatively inaccessible parts of the gut such as the cecum (accessed via the anus) and the distal jejunum and ileum (accessed via the mouth).

In one embodiment of the invention there are precisely two guide wires connected to one another at their leading ends. For many purposes, two wires are believed to be sufficient. However, in some circumstances more than two wires may be appropriate, and the present invention envisages that the guide wire structure may have three wires, four wires, or even more than four wires.

BRIEF DESCRIPTION OF DRAWINGS

The invention is described further below with reference to the accompanying drawings, in which.

DETAILED DESCRIPTION

Figure 1A:
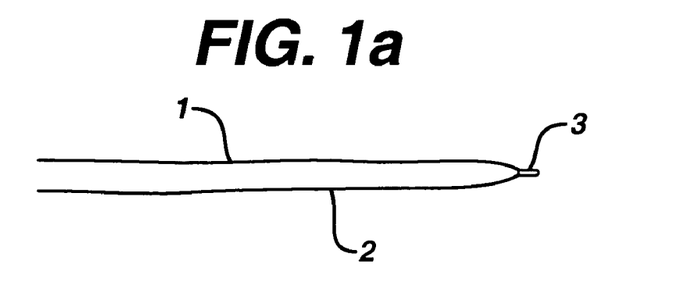
FIG. 1a shows an embodiment of guide wire structure according to the present invention in the condition which it tends to adopt when not in use.

The structure of FIG. 1a comprises a first guide wire 1 and a second guide wire 2, the wires 1 and 2 being connected to one another by a junction 3 formed at the leading ends of the wires 1 and 2. Although the junction 3 is shown as being at the leading ends, it could alternatively be adjacent the leading ends. The length of the junction need be no more than is necessary to hold the leading ends securely together side by side. Depending on the nature of the junction, a length of as little as 5-10 mm may be sufficient, though a greater length may sometimes be preferable.

The guide wires 2 and 3 can be made of the materials conventionally used for guide wires, for example straight stainless steel wire, coiled stainless steel wire, glass fiber, a plastics material, or nitinol. Conveniently, a guide wire has a floppy tip, i.e. a leading end portion, typically 4-5 cm in length, of greater flexibility than the remainder of the guide wire, in order to reduce the risk of the leading end of the guide wire causing damage to the wall of the lumen through which it is passing. Where two such conventional guide wires are joined together to produce the guide wire structure of the present invention, it will of course be these floppy tips, or parts thereof, which are joined together. Preferably, the length of the junction is less than the length of the floppy tips, so that some length of floppy material remains which is unaffected by the junction.

The whole or part of each of the guide wires may be coated to reduce its coefficient of friction, as is done with conventional guide wires. For example, guide wires can be coated with a low friction material such as silicone, or with a hydrophilic material which becomes slippery in use in a patient, or with both a low friction material such as silicone and hydrophilic material applied over the low friction material.

The junction 3 can be formed in any desired manner, provided the resulting leading end of the guide wire structure is not such as to damage the wall of the GI tract or other body lumen, nor cause undue pain when in contact therewith. For example, the junction can be made by gluing or welding the leading end portions together and, preferably, then covering those portions with heat shrink tubing. Alternatively, the end portions could be held together by having a metal band crimped on to them, optionally enclosed by a cover made of a softer material.

It is not essential for all the guide wires, or both the guide wires, as the case may be, to be of material which would normally be regarded as guide wire material. For example, in the case of a guide wire structure consisting of just two guide wires, one of the guide wires may be made of a thread, which is joined to the other guide wire by being tied to it.

Yet another possibility would be to start with a single guide wire of twice the required length and fold it sharply back on itself, for example by crimping the folded wire adjacent the fold, so that it became, in effect, a pair of guide wires joined at the fold. A guide wire structure having an even number n of guide wires greater than two could be formed by folding half that number of guide wires.

Figure 1B:
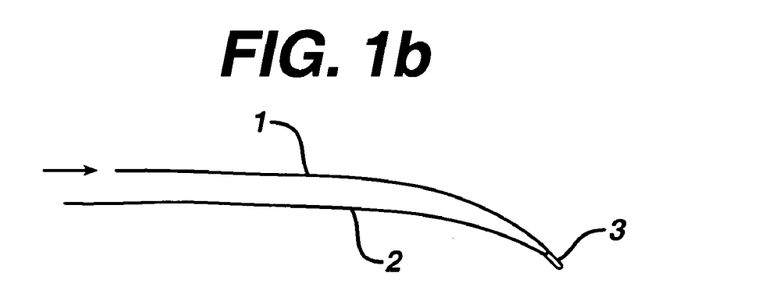
FIG. 1b shows the structure of FIG. 1a when one of its guide wires is advanced rightwardly and the other is held steady.
Figure 1C:
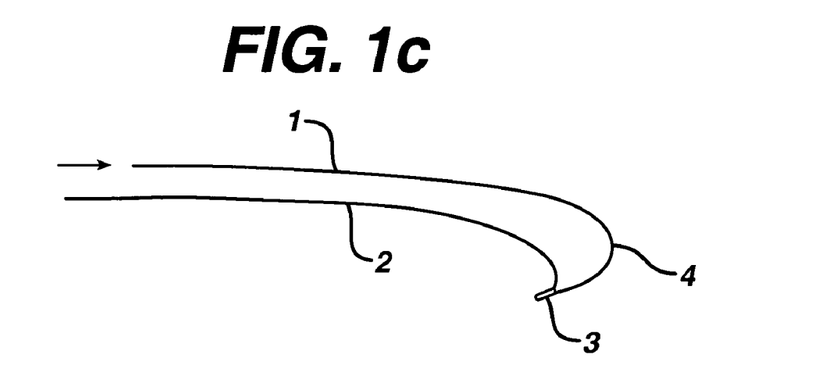
FIG. 1c shows the structure of FIG. 1a after further righthand advance of one of the guide wires.

The principle of operation of the guide wire structure can be seen by comparing FIGS. 1b and 1c with FIG. 1a. FIG. 1b shows the result of advancing the guide wire 1 rightwardly, as indicated by the arrow, whilst holding the guide wire 2 still. As indicated in FIG. 1b, this causes the distal region of the guide wire structure to curve in a direction so that the advanced guide wire 1 is on the outside of the curve and the still guide wire 2 is on the inside of the curve. Continued advancement of guide wire 1 beyond the position illustrated in FIG. 1b, whilst continuing to hold guide wire 2 steady, results in the formation of a loop in an end region of guide wire 1. This is illustrated in FIG. 1c, where the loop is denoted by reference numeral 4.

To enable the physician to easily advance one of the guide wires while keeping the other still, the guide wires are preferably received, at their ends remote from the junction 3, in a handle which can be moved up and down the guide wires as they are advanced and retracted. The handle should allow precise regulation of the relative lengths of the two guide wires. It should also allow the introduction of the various catheters, imagers and other accessories, discussed in more detail below, giving accurate information on their relationship to the junction 3. The handle may be provided with a reversible motor drive which enables both guide wires to be driven. The motor drive itself may provide data to enable the user to monitor the lengths of the guide wires which have been fed forward.

Figure 4:
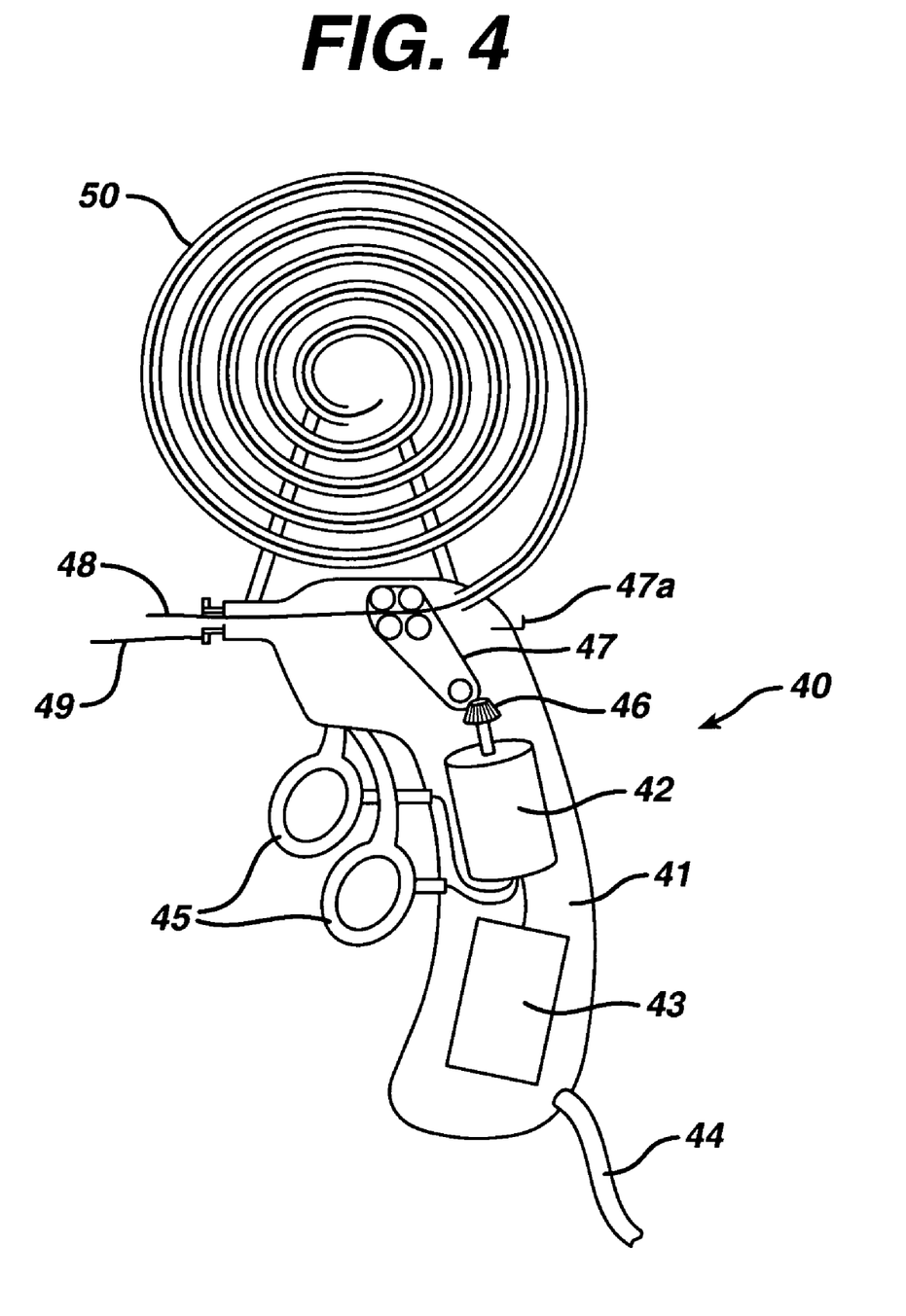
FIG. 4 shows diagrammatically a handle for use in controlling movement of the guide wires.

An example of a handle is illustrated in FIG. 4. The illustrated handle 40 comprises a pistol grip 41 within which is mounted a pair of electric motors 42 (of which one is shown) powered either by a battery 43 or a mains supply 44. The motors are controlled by respective finger controls 45, one for each motor, each control having forward, reverse and stop positions. Each motor provides drive, via a respective gear, shown diagrammatically at 46, to a respective belt or chain drive 47, each of which propels a respective guide wire 48 forwardly (or backwardly). A switch 47a is provided to cause the driving belts or chains to move away from the wires, to allow the wires to be released, for example at the conclusion of a procedure. A lock mechanism 49 is provided to attach the handle 40 to a catheter or to an accepting channel of an endoscope, through which the guide wire is to be driven. The guide wires are stored in a coiled plastics tube 50, either with both wires side by side in a single tube or each in its own tube. This has the benefit of keeping the guide wires clean, and avoiding the risk of their trailing on to the floor. Under some conditions this storage facility may be omitted.

The combined effect of the forms of behaviour illustrated in FIGS. 1b and 1c enables the guide wire structure of the present invention to perform in a highly advantageous manner. Thus, causing the structure to become curved, as shown in FIG. 1b, enables the physician to steer the leading end of the structure round bends in the lumen through which the structure is being advanced. The ability to form a loop, as illustrated in FIG. 1c, enables the guide wire structure to adopt as configuration in which it can be safely advanced along the lumen, without undue discomfort for the patient.

Furthermore, the presence of a loop at the leading end of the structure rather than the tip of a single wire, makes the structure more likely to follow the main course of the lumen, and less likely to inadvertently enter branches off it. Thus, in the case of the gut, there will be a much reduced tendency to enter, for example, diverticulae or the orifice of the appendix. However, the fact that the loop is not permanently present, and can be eliminated by putting the structure into the configuration shown in FIG. 1a, means that the structure can easily, and without damage to itself, be passed along a very narrow passageway. It can therefore be passed, for example, along a channel of an endoscope or down a catheter, as is described further below. Also, when the guide wire structure is not in an endoscope or catheter, but is advancing directly along a patient lumen, it is not always desirable to do so with a loop at the front (for example if it has to pass through a small opening). Under such circumstances the guide wire structure is allowed to revert to the straight form shown in FIG. 1a with both guidewires being advanced aligned and in unison.

Figure 3A:
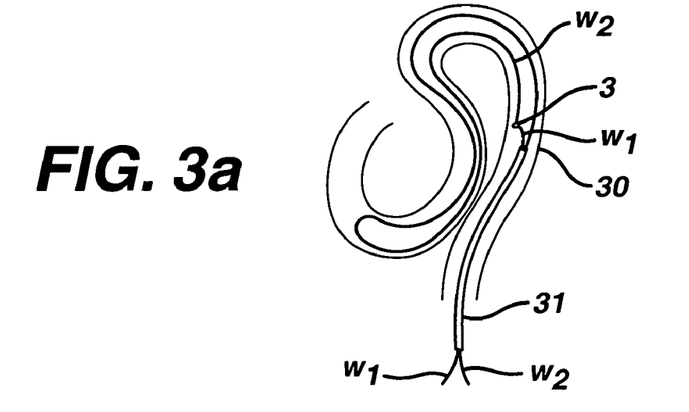
FIGS. 3a to 3c show a guide wire structure according to the invention advancing into the colon.
Figure 3B:
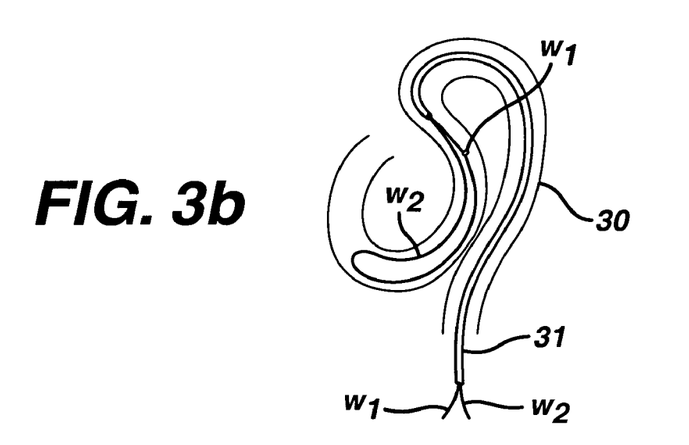
Figure 3C:
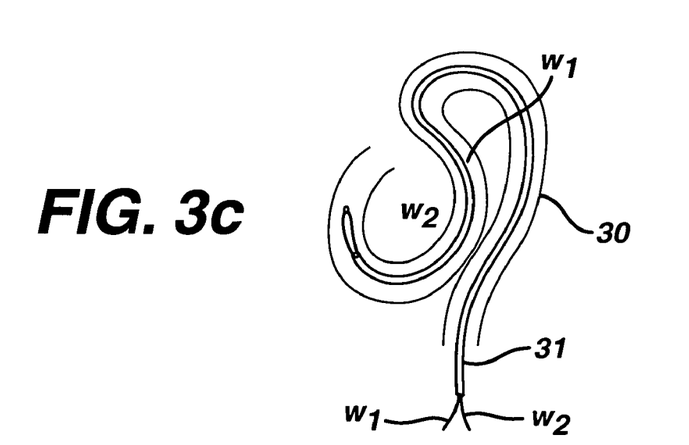

FIGS. 3a to 3c show diagrammatically, and by way of example, successive stages in advancing the guide wire structure of the invention along a colon 30. It is shown being introduced in conjunction with a catheter 31 within which the whole guide wire structure is slidably received. The individual guide wires are denoted as $w_1$ and $w_2$. Advancement takes place by alternately:

(a) pushing one wire forward while holding the other still; and
(b) pushing the catheter forwards as far as the position shows in FIG. 3c, or even somewhat further.

Figure 2:
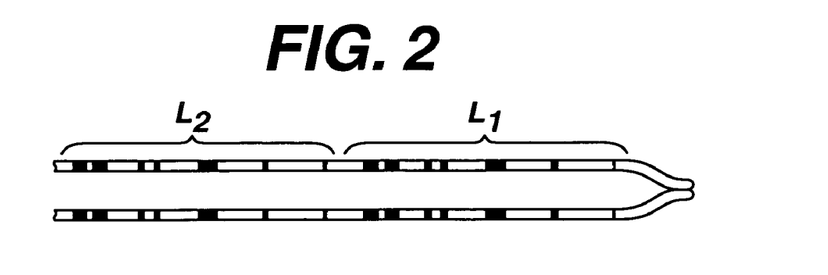
FIG. 2 shows an example of a pattern of markings which may be provided on the guide wires to indicate their relative position to a physician.

It is desirable in endoscopic procedures to avoid, or at least reduce, the use of X-ray imaging to monitor what is taking place. With this in mind, the guide wires are preferably each provided with a pattern of markings, distributed along their length, to indicate how far each individual guide wire has been inserted. One such pattern in shown in FIG. 2. As shown there, a pattern of markings in a given colour, and similar in nature to a bar code, is spaced along a first length ($L_1$), and then repeated along successive lengths (of which only $L_2$ is shown) each time in a different colour. Each of the lengths could conveniently be of the order of 10 cm. This provides a method by which the physician can easily see which of the guide wires is the further advanced, and by how much, and enable him, for example, to make the inserted lengths equal and thus eliminate any curve (FIG. 1b) or loop (FIG. 1c). Of course, many other patterns of marking, for example numerals or letters, could be used instead of that illustrated, which is given only as an example.

Additionally, or instead, the guide wire structure can be provided with other forms of position indication. It is known to provide a conventional guide wire with a series of miniature electrically conductive coils which surrounded the guide wire and are spaced along its length, the coils being connected to a source of electrical current, whereby each coil becomes a miniature electromagnet. Such coils can be provided on the guide wires used to form the guide wire structure of the present invention. A sensing device outside the patient is used to detect the position of the coils within the patient, and thereby determine the location of the guide wires.

Figure 5A:
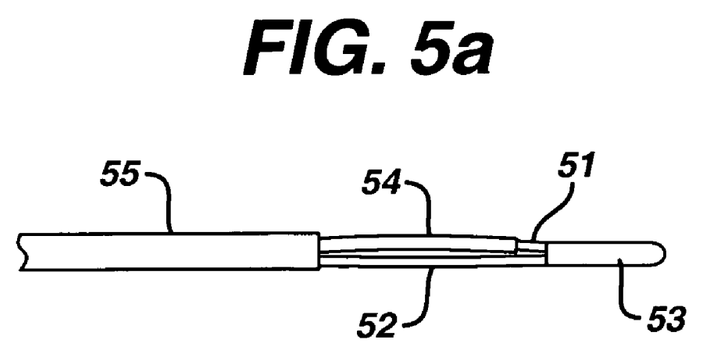
FIGS. 5a and 5b show successive stages in the use of the guide wire structure of the present invention in conjunction with a bias tube.
Figure 5B:
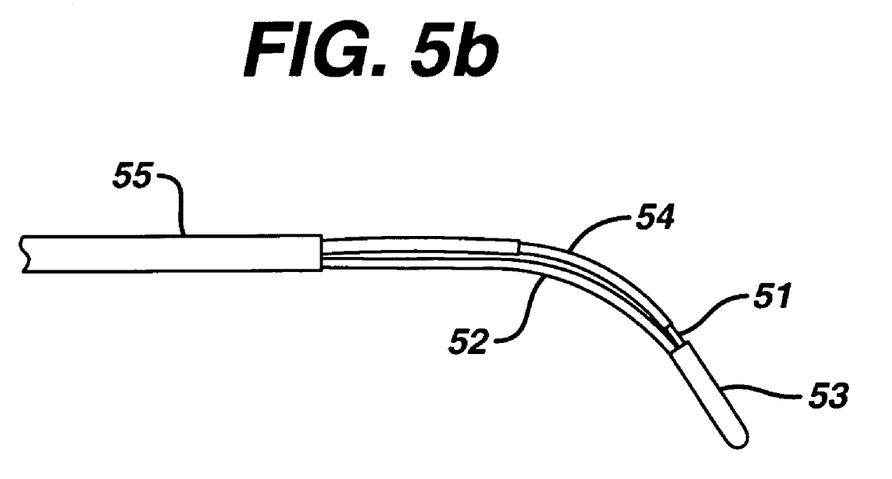

The path of the guide wire structure can be influenced by the use of a catheter, which can be passed over one or both of the two guide wires, when there are precisely two, or over one, some, or all of the guide wires, when there are more than two. In one particularly advantageous embodiment the catheter has a curved tip, which allows the application of torque to bias the forward motion of the guide wire (or wires) over which it passes in any given direction. The use of a catheter in this way is illustrated in FIGS. 5a and 5b. FIGS. 5a and 5b show a pair of guide wires 51 and 52 joined at a junction 53. Guide wire 51 is received within a catheter 54, referred to herein as a bias tube, the leading end portion of which is so formed as to have a curvature in it. The guide wire 51 with the bias tube, and the guide wire 52, are both received within an outer catheter 55. The ends of the catheters 51 and 52 remote from their tips emerge from the catheter 55 to allow them to selectively advance and retract. The end of the bias tube 54 remote from the curved end thereof emerges from the outer catheter 55 at the user's end. As can be seen by comparing the state shown in FIG. 5a with the subsequent state shown in FIG. 5b, in advancing both the guide wires, but advancing guide wire 51 more than guide wire 52, the bias tube helps to ensure that the combined guide wire structure curves in the desired direction. If it were desired to cause the structure to advance in some other direction, this could be achieved by twisting the catheter 55 about its longitudinal axis, thus altering the positions of the guide wires relative to the lumen in which they are being advanced.

The purpose of the guide wire is, as its name indicates, to act as a guide for some other element. Accordingly, when the guide wire structure of the present invention is in place some other element is then passed over it.

As in the case of a catheter used to influence the path of a guide wire structure during passage of the guide wire structure along a lumen, a catheter introduced subsequently can pass over one or both of the guide wires, when there are precisely two, or over one, some, or all of the guide wires, when there are more than two. When the catheter is passed over both, or all, the guide wires, as the case may be, the leading end of the catheter will be free to pass beyond the leading end of the guide wire structure once it reaches that point. If the catheter is not passed over both, or all, the guide wires, for example if it is passed over only one of two interconnected guide wires, the leading end of the catheter will normally be unable to pass beyond the connection between the guide wires. That may be desirable, for the purpose of ensuring that the leading end of the catheter can be brought to a position previously defined by the leading end of the guide wire structure. It also has the result, however, that if the guide wire structure is withdrawn, the catheter must be withdrawn with it.

Figure 6A:
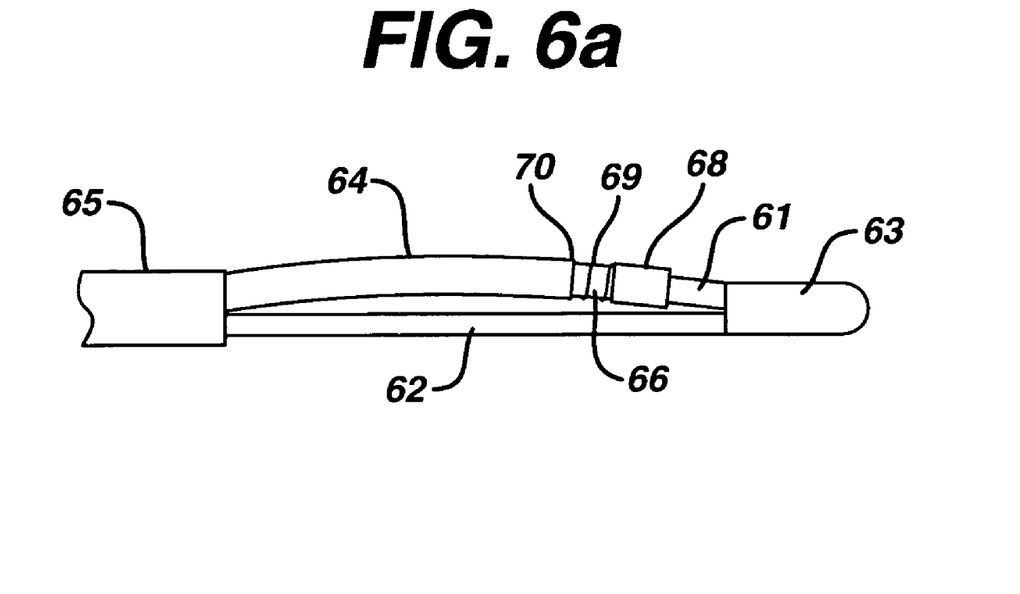
FIGS. 6a and 6b show successive stages in the use of a cutting catheter to sever the junction between two guide wires.
Figure 6B:
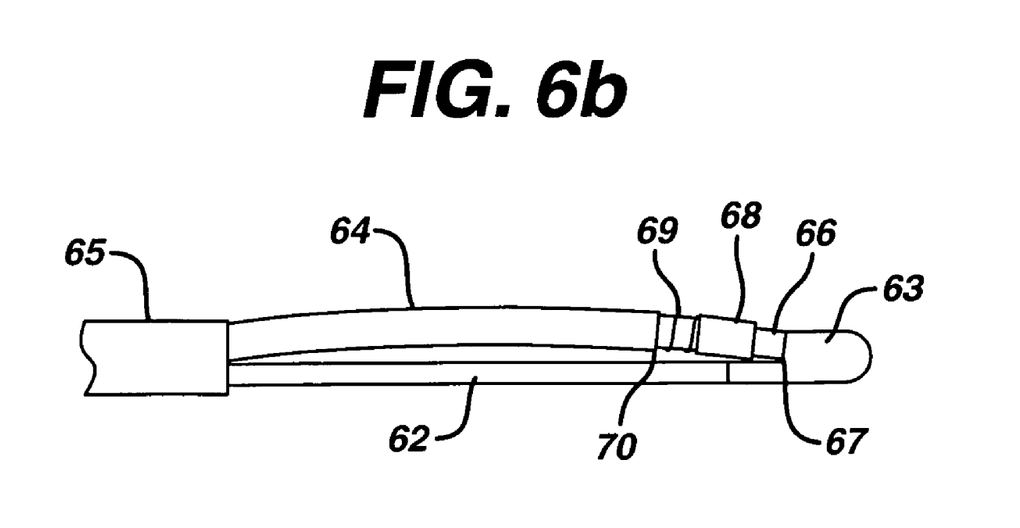

If it is desired to enable the leading end of the catheter to pass beyond the end of the guide wire over which it is travelling, or to enable the catheter to remain in position after the guide wire has been withdrawn, this can be achieved by providing the leading end of the catheter with a cutting device. The use of such a catheter is illustrated in FIGS. 6a and 6b. FIGS. 6a and 6b show guide wires 61 and 62 connected by a junction 63 and extending within an outer catheter 65. A cutting catheter 64 surrounds one of the guide wires, in this case the guide wire 61. The catheter 64 has a cutting tip (not visible in FIG. 6a) which, when the catheter 64 is advanced over the guide wire 61, severs the junction 63. FIG. 6b shows the severing operation partly completed.

The cutting catheter comprises a cylindrical cutting member 66 with a circular cutting edge 67 (visible in FIG. 6b but not in FIG. 6a) formed at its leading end. When not in use the cutting edge is shielded by a generally cylindrical sheath 68 which is biased to a forward protecting position by a compression spring 69 located between the rearward end of the sheath 68 and a stop 70 fixed to the end of the catheter. When the cutting catheter is pushed forwards, against the force of the spring 69, as it is in FIG. 6b, the cutting edge 67 emerges from the sheath 68 and severs the junction 63. As soon as severing is completed the spring automatically causes the sheath 68 to move forwards, covering the cutting edge 67 and preventing it from harming the patient.

Once a sufficiently large guide wire loop has been formed in, say, the gut, it becomes possible to pull the gut backwards to some extent, using the friction between the loop and the wall of the gut. To do this, both guide wires are pulled backwards in synchronism. This provides a means for straightening the gut, and this in turn makes it easier to advance the guide wire structure further or, indeed, to advance other structures (e.g. endoscopes), and reduces the pain of the procedure, which is mainly caused by stretching nerve endings in the mesentery.

Figure 7:
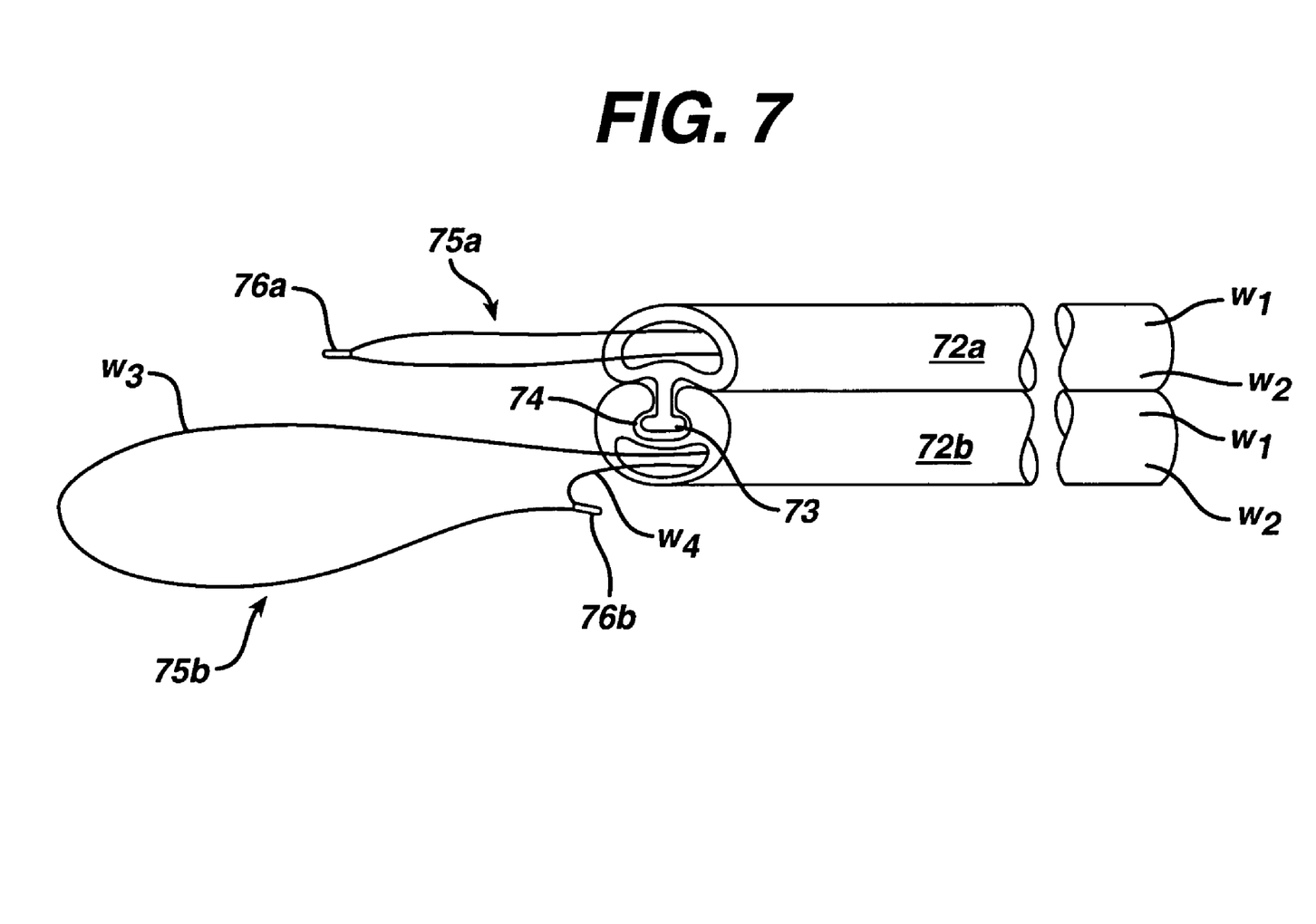
FIG. 7 shows an embodiment of the invention which comprises two guide wire structures arranged in parallel.

The above described concept of using a guide wire loop to straighten a passageway, e.g. the gut, can be further developed in an embodiment of the present invention which employs two guide wire structures operating in parallel. An example of such an embodiment is shown in FIG. 7. This comprises two parallel catheters 72a and 72b, which are preferably connected together side by side in such a way as to allow each to move longitudinally with respect to the other. In the illustrated embodiment the connection is provided by a T-shaped stud 73 formed on catheter 72a which is slidable in a correspondingly shaped passageway 74 formed in catheter 72b and running longitudinally along it. A single stud may be provided, or a plurality of studs spaced along the length of catheter 72a, or there may be a continuous stud running along all or part of the length of catheter 72a. Catheter 72a receives a first guide wire structure 75a, comprising a pair of wires $w_1$ and $w_2$ joined at a junction 76a. Catheter 72b receives a guide wire structure 75b, comprising a pair of wires $w_3$ and $w_4$ joined at a junction 76b.

The embodiment shown in FIG. 7 can be used in a procedure which employs the following steps:
1. Push the combination of catheters 72a and 72b into an appropriate orifice, e.g. the anus in the case of the colon, as far as they will go.
2. Advance wire $w_3$ as far as the loop which it forms is able to travel (this is substantially the configuration shown in FIG. 7).
3. Pull back on both catheters so that the loop in guide wire structure 75b straightens the gut.
4. Advance guide wire structure 75a in its unlooped form, i.e. wires $w_1$ and $w_2$, through the catheter 72a as far as it will go (which should be past the loop in guide wire structure 75b).
5. Advance catheter 72a over $w_1$ and $w_2$ so that it is ahead of catheter 72b, while catheter 72a, and the loop extending from the catheter, hold the gut in position.
6. Advance guide wire $w_1$ or guide wire $w_2$ so that a loop is formed in guide wire structure 75a and advances in the gut.
7. Withdraw whichever of wires $w_3$ and $w_4$ is the more forward of the two, so as to eliminate the loop in guide wire structure 75b. 5
8. Advance catheter 72b so that it catches up with catheter 72a.

The above cycle is then repeated until the desired degree of advancement has been achieved.

A similar cycle of steps can be achieved by a modified form of the embodiment of FIG. 7, in which one or each of the two catheters 72a and 72b is replaced by a suction catheter. A suction catheter can be used to effect the above described straightening of the gut by pulling back on it while suction is being applied. The suction is only applied during the straightening step. Yet another modification is to replace one of the guide wire structures by a soft balloon, which can be inflated to engage the gut wall, and then pulled back to straighten the gut.

Many different devices can be passed over the guide wire structure, and some examples will now be given.
(a) A small imager (for example a CCD or CMOS chip) on a catheter could be passed along the guide wire or guide wires to the tip. This could optionally be propelled along the guide wire by a water jet or some other means of tip propulsion to reduce the force that has to be exerted outside the patient. A source of white or coloured light could be also introduced by the same means. This source could be in the form of light emitting diodes or could use fibre-optics. One of the wires could be optionally formed out of a fiberoptic bundle. It would be easier to take the optical signal through a light-weight insulated wire which could be incorporated into the guide wire or via a separate wire in a catheter. The imager could then convert the optical information to radiowaves or microwaves, to send the information to an aerial attached to, or adjacent to, the exterior of the patient.
(b) A separate soft catheter could be run over the guide wire to the tip and this could be used to introduce air from a controlled pump to inflate the viscus. Water for rinsing purposes could be passed through this catheter or through some other from a water pump.
(c) A catheter could be passed over one of the guide wires, which would provide a channel through which biopsies could be performed. This is preferably done after the imager referred to in (a) above has been placed in position, so that the imager can be used to view the biopsy procedure. This catheter might have tip angulation properties.
(d) A double lumen catheter could be passed over the double wire, which might allow the introduction of another wire of greater stiffness or with a curled tip to allow the movement of the device in a desired direction.

Once the guide wire, and the imager referred to in (a) above, have reached the desired location, an overtube could be passed, for example to the cecum. The guide wire and the imager could then be withdrawn and a conventional endoscope could be passed through the overtube to deliver therapy, for example removing a polyp or cancer.

A conventional endoscope could be introduced into a body lumen by passing it over the guide wire structure of the present invention. However, a conventional endoscope would normally be too stiff for this to be possible, and the guide wire structure of the present invention offers the possibility of, in effect, constructing an endoscope within a patient. To achieve this, a number of catheters, each providing one or more of the utilities normally provided a conventional endoscope, are successively passed over one or more of the guide wires, so that result is an assemblage of these various elements within the patient. A particular advantage of proceeding in this way is that the force required to advance each of the individual catheters is substantially less than that required to advance a complete conventional endoscope (e.g. a colonoscope or an enteroscope), since the latter is much stiffer and has much greater mass. It is therefore easier for the physician, and less uncomfortable for the patient, and is less likely to cause injury to the patient. Also, since the endoscope is then assembled element by element, the endoscope can have those facilities which are required for the particular patient, and, only those facilities, so that the endoscope is tailored to the requirements of the medical procedure being carried out. It will be understood that, for the purpose of allowing in situ assembly of a catheter, the guide wire structure should preferably comprise more than two guide wires, for example three or four guide wires.

Although a structure having more than two guide wires is particularly useful for the purpose discussed above of assembling an endoscope in situ, it may also have value in relation to the procedure for introducing the guide wire structure into a lumen. This is because the two-guide wire structure shown in FIGS. 1a to 1c allows curvature in only one plane, so that steering the structure in three dimensions requires the user to twist the structure about its longitudinal axis, for example by using a catheter to which the necessary torque can be applied. However, if more than two guide wires are provided it is possible to curve the structure in any plane; three guide wires are sufficient for this purpose.

Figure 8A:
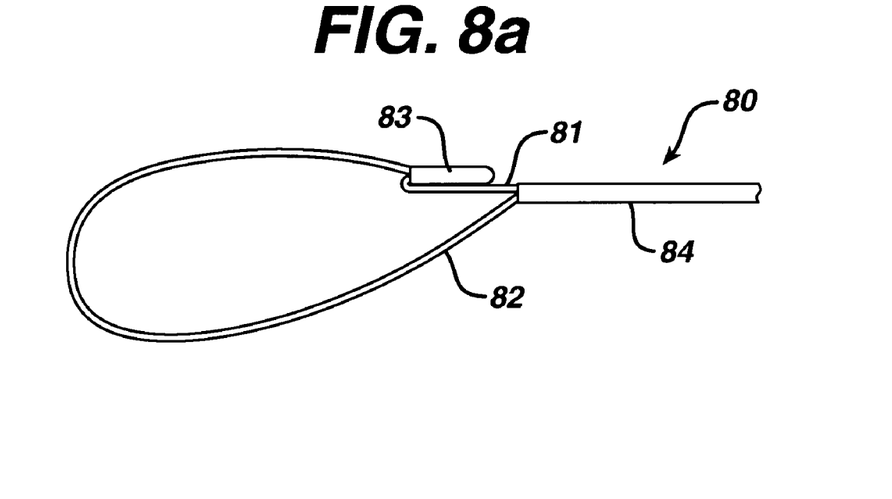
FIGS. 8a to 8c illustrate diagrammatically the use of a guide wire structure according to the present invention, which has a pivotal junction portion.
Figure 8B:
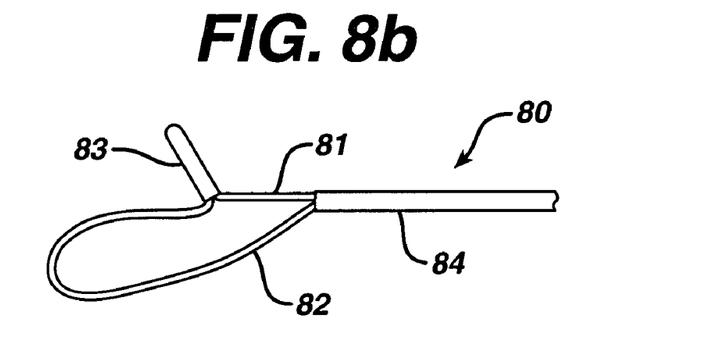
Figure 8C:
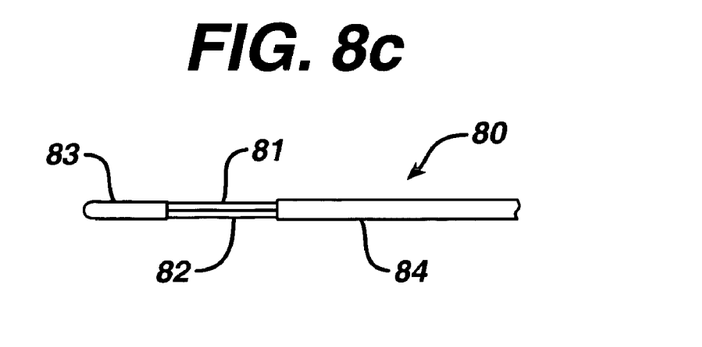

Attention is now directed to FIGS. 8a to 8c, which illustrate the use of a guide wire structure 80 which comprises two guide wires 81 and 82 connected by a junction portion 83. As can be seen, the junction portion 83 is pivotal about an axis located at the proximal end of the portion 83, so that, as shown in FIG. 8a, it can pivot to such an extent that it lies flat along the distal end portion of guide wire 81. This is advantageous in that it makes possible, or makes easier, movement of the portion 83 within a catheter 84, not only where there is no loop present (as in FIG. 8c) but also when there is (as shown in FIG. 8a). In this connection it is to be understood that the diameter of the catheter 84 would actually be substantially greater than that shown in these Figures. It is also to be understood that instead of being joined by a junction portion 83 of significant length, as illustrated, the guide wires could alternatively be joined by a junction of substantially no length, i.e. the ends of the guide wires could be connected by a junction consisting, at least in substance of just a pivot point.

Figure 9:
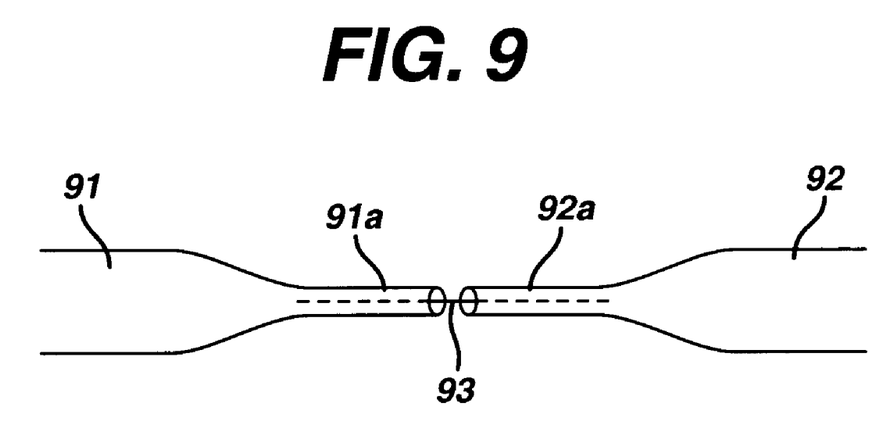
FIG. 9 shows yet another guide wire structure according to the present invention.

FIG. 9 shows yet another guide wire structure in which a similar pivoting action can be achieved. This comprises guide wires 91 and 92, having respective floppy tip portions 91a and 92a connected to one another by a thread or highly flexible wire 93. This thread or wire can be inserted into the portions 91a and 92a, or attached to their surfaces.

The invention claimed is:

1. A guide wire structure for insertion into an interior space defined by a wall, the guide wire structure comprising at least two guide wires each having a leading end portion which terminates in a leading end, the guide wires being connected to one another by a junction at or adjacent their leading ends, wherein at least one of the guide wires is received in an individual catheter provided at a leading end thereof with a cutter arranged to cut through the said junction, the guide wires have a first position in which the leading end portions are substantially parallel to one another, a second position in which the leading end portions are curved, and a third position in which at least one of the leading end portions forms a loop, wherein the said junction is covered with heat shrink tubing.

2. The guide wire structure of claim 1, wherein the said junction is formed by gluing.

3. A guide wire structure according to claim 1, wherein the said junction is formed by welding.

4. A guide wire structure according to claim 1, wherein the number of guide wires is an even number n, and the structure is formed by folding n/2 longer guide wires, each having twice the length desired for the structure, sharply back.

5. A guide wire structure according to claim 1, wherein the said individual catheter has a leading end portion which is curved.

6. A guide wire structure for insertion into an interior space defined by a wall, the guide wire structure comprising at least two guide wires each having a leading end portion which terminates in a leading end, the guide wires being connected to one another by a junction at or adjacent their leading ends, wherein at least one of the guide wires is received in an individual catheter provided at a leading end thereof with a cutter arranged to cut through the said junction, the guide wires have a first position in which the leading end portions are substantially parallel to one another, a second position in which the leading end portions are curved, and a third position in which at least one of the leading end portions forms a loop, wherein the said junction is formed by a metal band crimped over the guide wires.

7. A guide wire structure according to claim 6, wherein the said metal band is enclosed by a cover formed of a softer material.

8. A guide wire structure for insertion into an interior space defined by a wall, the guide wire structure comprising:
a first pair of guide wires received in a first catheter each having a leading end portion which terminates in a leading end, the guide wires being connected to one another by a first junction at or adjacent their leading ends;
a second pair of guide wires received in a second catheter each having a leading end portion which terminates in a leading end, the guide wires being connected to one another by a second junction at or adjacent their leading ends;
the first and second pair of guide wires each having a first position in which the leading end portions are substantially parallel to one another, a second position in which the leading end portions are curved, and a third position in which at least one of the leading end portions forms a loop.

9. A guide wire structure according to claim 8, wherein the first and second catheters are connected to one another in such a way as to permit longitudinal movement of each catheter relative to the other.

10. A guide wire structure according to claim 9, further comprising an user-controllable handle for advancing and retracting each of the guide wires.

11. A guide wire structure according to claim 10, wherein the handle comprises a guide wire storage device.

12. A guide wire structure according to claim 8, adapted for use in the human gastrointestinal tract.

13. A guide wire structure for insertion into an interior space defined by a wall, the guide wire structure comprising at least two guide wires each having a leading end portion which terminate in a leading end, the guide wires being connected to one another by a junction at or adjacent their leading ends, wherein at least one of the guide wires is received in an individual catheter provided at a leading end thereof with a cutter arranged to cut through the said junction, the guide wires have a first position in which the leading end portions are substantially parallel to one another, a second position in which the leading end portions are curved, and a third position in which at least one of the leading end portions forms a loop, wherein a shield is disposed at the said catheter leading end, the said shield being movable between a shielding position in which it surrounds the said cutter, and a non-shielding position in which the said cutter is exposed for use.

14. A method of inserting the guide wires structure of claim 8 into the human gastrointestinal tract, comprising steering the guide wires through the tract by selectively advancing or retracting a single guide wire or advancing more than one guide wire simultaneously, according to the path which is required to be followed.

* * * * *